United States Patent [19]

Flynn et al.

[11] Patent Number: 5,252,601

[45] Date of Patent: Oct. 12, 1993

[54] 2-MERCAPTOMETHYLENE-TETRAHYDRONAPHTHALENE AND INDANE-2-CARBOXAMIDE DERIVATIVES AS ENKEPHALINASE INHIBITORS

[75] Inventors: Gary A. Flynn; Douglas W. Beight, both of Cincinnati, Ohio

[73] Assignee: Merrell Dow Pharmaceuticals Inc., Cincinnati, Ohio

[21] Appl. No.: 860,572

[22] Filed: Apr. 3, 1992

Related U.S. Application Data

[63] Continuation-in-part of Ser. No. 695,635, May 3, 1991, abandoned.

[51] Int. Cl.$^5$ .................. A61K 31/36; A61K 31/195; C07D 321/00; C07D 321/06; C07C 233/58

[52] U.S. Cl. .................. 514/465; 435/183; 514/510; 514/562; 514/618; 549/407; 560/10; 560/16; 562/426; 562/427; 562/428; 564/162

[58] Field of Search .................. 560/10, 16; 564/162; 562/426, 427, 428; 514/510, 465, 562, 618; 549/407; 435/183

[56] References Cited

U.S. PATENT DOCUMENTS

| | | | |
|---|---|---|---|
| 4,973,585 | 11/1990 | Flynn et al. | 514/214 |
| 4,975,460 | 12/1990 | Iwakuma et al. | 514/510 |

Primary Examiner—José G. Dees
Assistant Examiner—Vera C. Clarke
Attorney, Agent, or Firm—Charlotte L. Barney

[57] ABSTRACT

The present invention relates to novel 2-mercaptomethylene-tetrahydronaphthalene derivatives which are useful as enkephalinase inhibitors.

25 Claims, No Drawings

2-MERCAPTOMETHYLENE-TETRAHYDRONAPHTHALENE AND INDANE-2-CARBOXAMIDE DERIVATIVES AS ENKEPHALINASE INHIBITORS

This application in a continuation-in-part of application Ser. No. 07/695,635, filed May 03, 1991, now abandoned.

BACKGROUND OF THE INVENTION

Enkephalinase or, more specifically, neutral endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would be useful in providing an antidiarrheal effect in a patient suffering therefrom.

ANP refers to a family of naturally-occurring peptides which are involved in the homeostatic regulation of blood pressure, as well as sodium and water levels. ANP's have been found to vary in length from about 21 to about 126 amino acids with a common structural feature being one or more disulfide-looped sequences of 17 amino acids with various amino- and carboxy-terminal sequences attached to the cystine moiety. ANP have been found to bind to specific binding sites in various tissues including kidney, adrenal, aorta, and vascular smooth muscle with affinities ranging from about 50 pico-molar (pM) to about 500 nanomolar (nM) [Needleman, Hypertension 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, Science, 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

By inhibiting enkephalinase, a cognition enhancing effect is also provided in patients suffering from disease states such as Alzheimer's Disease.

SUMMARY OF THE INVENTION

The present invention provides novel compounds of the formula (I)

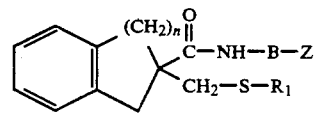

wherein
n is an integer 2,
Z is the radical —C(O)OR, or a phenyl group unsubstituted or substituted with from 1 to 3 substituents selected from the group consisting of OH, $C_1$-$C_4$ alkoxy, and methylenedioxy,
R is H, $C_1$-$C_4$ alkyl, or benzyl,
$R_1$ is H or —C(O)—A, wherein A is $C_1$-$C_4$ alkyl, or phenyl, and
B is a radical of the formula

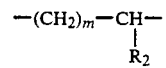

or

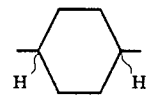

wherein
m is an integer 0 to 5, and
$R_2$ is H, $C_1$-$C_4$ alkyl, —$CH_2$—OH, —CH(OH)—$CH_3$, —$CH_2CH_2SCH_3$, phenylmethyl, 4-hydroxyphenylmethyl or OH, with the proviso that $R_2$ cannot be OH when m is 0.

These compounds are useful as inhibitors of enkephalinase.

The present invention further provides a method of inhibiting enkephalinase in a patient in need thereof comprising administering to said patient an effective enkephalinase inhibitory amount of a compound of formula (I).

In addition, the present invention provides a composition comprising an assayable amount of a compound of formula (I) in admixture or otherwise in association with an inert carrier. The present invention also provides a pharmaceutical composition comprising an effective enkephalinase inhibitory amount of a compound of formula (I) in admixture or otherwise in association with one or more pharmaceutically acceptable carriers or excipients.

DETAILED DESCRIPTION OF THE INVENTION

The compounds of formula (I) are mercaptomethylene and carboxamide derivatives of a fused bicyclic moiety. The fused bicyclic moiety represented in formula (I) can be an indane moiety, when n is 1 or a tetrahydronaphthalene moiety, when n is 2.

As used herein, the term "$C_1$–$C_4$ alkyl" refers to a saturated straight or branched chain hydrocarbyl radical of one to four carbon atoms and specifically includes methyl, ethyl, propyl, isopropyl, n-butyl, isobutyl, sec-butyl, tertiary butyl and the like.

As used herein, the term "$C_1$–$C_4$ alkoxy" refers to an alkyloxy radical made up of an oxygen radical bearing a saturated straight or branched chain hydrocarbyl radical of one to four carbon atoms and specifically includes methoxy, ethoxy, propyloxy, isopropyloxy, n-butyloxy, isobutyloxy, sec-butyloxy, tertiary butyloxy and the like.

Z is defined as the radical —C(O)OR or a phenyl unsubstituted or substituted with from 1 to 3 substituents selected from the group consisting of OH, $C_1$–$C_4$ alkoxy, and methylenedioxy. The representation "—C(O)OR" refers to a carboxylic acid or ester functionality. When Z is a substituted phenyl moiety, the phenyl may be substituted in the ortho, meta or para positions with from 1 to 3 substituents. It is of course understood that where the phenyl is substituted with methylenedioxy, the methylenedioxy moiety is attached to adjacent carbon atoms of the phenyl ring. Specifically included within the scope of the term "Z" are —COOH, —COOCH$_3$, —COOCH$_2$CH$_3$, phenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 3,4-dimethoxyphenyl, 3,4-diethoxyphenyl, 2,3-methylenedioxyphenyl, 3,4-methylenedioxyphenyl, 3-hydroxy-4-methoxyphenyl and the like.

B is defined as a radical of the formula

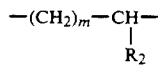

or

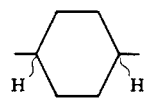

wherein
m is an integer 0 to 5, and
$R_2$ is H, $C_1$–$C_4$ alkyl, —CH$_2$—OH, —CH(OH)—CH$_3$, —CH$_2$CH$_2$SCH$_3$, phenylmethyl, 4-hydroxy-phenylmethyl or OH, with the proviso that $R_2$ cannot be OH when m is 0.

When B is the cyclohexylidene moiety, the amide linkage to B and the carboxy linkage to B are at the 1 and 4 positions of the cyclohexylidene moiety and are cis with respect to each other. When B is —(CH$_2$)$_m$CH(R$_2$)— and m is 0, the moiety thus formed, i.e., —NH—CH(R$_2$)—C(O)—O—, resembles a naturally occurring amino acid unit with $R_2$ representing the amino acid side chain.

Of course it is understood that the compounds of formula (I) may exist in a variety of isomeric configurations including structural as well as stereo isomers. These compounds can have one or more chiral centers. For example, the carbon in the bicyclic moiety to which the mercaptomethylene and the carboxamide groups attach, may exist in the (R) or the (S) form. In addition, the methylidene moiety of B may exist in the (R) or the (S) form. It is further understood that the present invention encompasses those compounds of formula (I) in each of their various structural and stereo isomeric configurations as individual isomers and as mixtures of isomers.

When $R_1$ is —C(O)—A, the compounds of formula (I) bear a thiocarboxy moiety. In other words, the structure of this moiety is

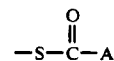

The partial structure formed by the designation —(CH$_2$)$_n$— represents a saturated hydrocarbyl radical of straight chain configuration having from 1 to 2 carbon atoms. The partial structure formed by the designation —(CH$_2$)$_m$— represents a saturated hydrocarbyl radical of straight chain configuration having from 0 to 5 carbon atoms.

The compounds of formula (I) can be prepared using techniques and procedures well known and appreciated by one of ordinary skill in the art. A general synthetic procedure for preparing these compounds is set forth in Scheme A. In Scheme A, all substituents unless otherwise indicated are as previously defined.

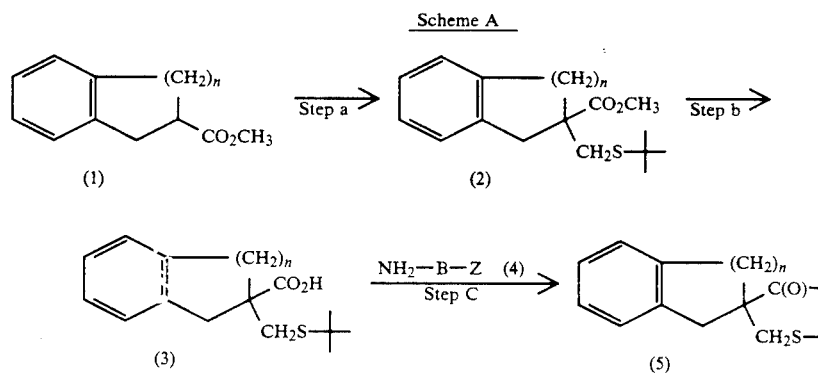

Scheme A

-continued

Scheme A

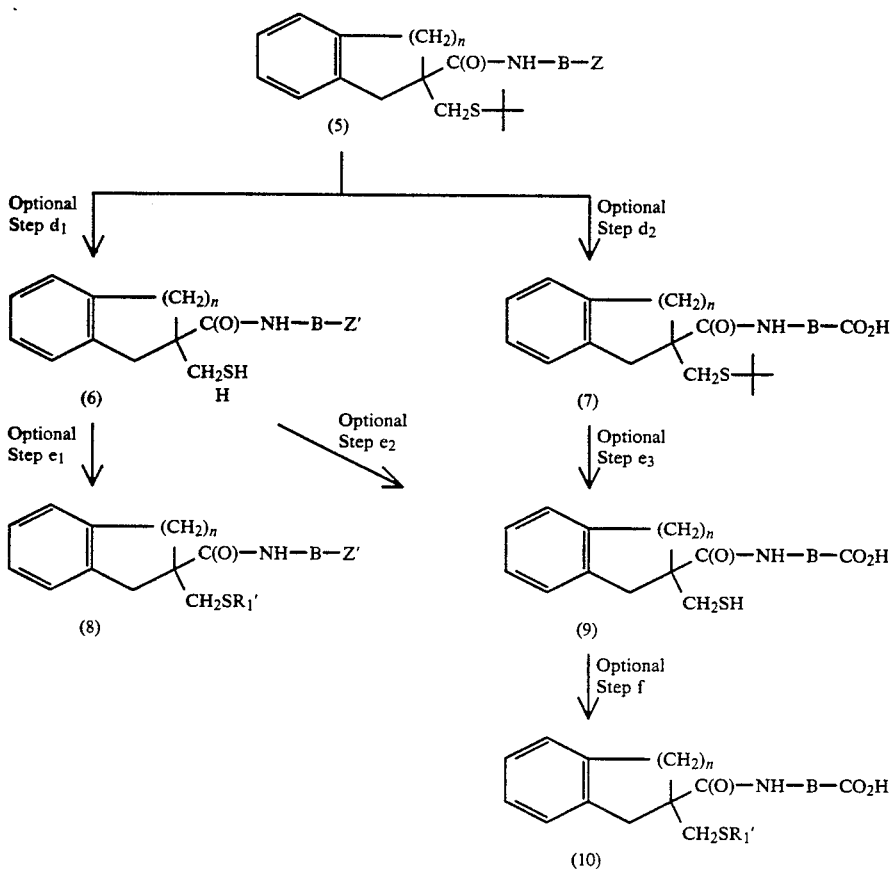

Z' = —COOR' wherein R' is $C_1-C_4$ alkyl or benzyl, or phenyl unsubstituted or substituted
$R_1'$ = —C(O)—A Scheme A provides a general synthetic procedure for preparing the compounds of formula (I).

In step a, the appropriate carbomethoxy substituted bicyclic compound of structure (1) is alkylated with t-butyl chloromethylsulfide to give the corresponding carbomethoxy-t-butylthiomethyl disubstituted bicyclic compound of structure (2).

For example, the appropriate carbomethoxy substituted bicyclic compound of structure (1) is first deprotonated with a molar equivalent of an appropriate non-nucleophilic base such as lithium diisopropylamide. The reactants are typically contacted under anhydrous conditions in a suitable aprotic organic solvent such as tetrahydrofuran. The reactants are typically stirred together for a period of time ranging from 15 minutes to 5 hours and at a temperature range of from −20° C. to −70° C. A molar equivalent of trimethylsilyl chloride is then added. The reaction mixture is stirred for a period of time ranging from 1-30 minutes at a temperature range of from −70° C. to 10° C. The intermediate silyl ketene acetal is recovered from the reaction zone by evaporation of the solvent. The intermediate silyl ketene acetal is then contacted with a catalytic amount of zinc bromide followed by a molar equivalent of t-butyl chloromethylsulfide. The reactants are typically contacted in a suitable organic solvent such as methylene chloride. The reactants are typically stirred together for a period of time ranging from 15 minutes to 1 hour. The carbomethoxy-t-butylthiomethyl disubstituted bicyclic compound of structure (2) is recovered from the reaction zone by extractive methods as is known in the art. It can be purified by silica gel chromatography and recrystallization.

In step b, the methyl ester of the appropriate carbomethoxy-t-butylthiomethyl disubstituted bicyclic compound of structure (2) is hydrolyzed to give the corresponding carboxy-t-butylthiomethyl disubstituted bicyclic compound of structure (3).

For example, the appropriate carbomethoxy-t-butylthiomethyl disubstituted bicyclic compound of structure (2) is contacted with a molar excess of an appropriate base such as lithium hydroxide. The reactants are contacted in a suitable protic solvent such as methanol. The reactants are typically stirred together for a period of time ranging from 1-24 hours and at a temperature range of from room temperature to reflux. The carboxy-t-butylthiomethyl disubstituted bicyclic compound of structure (3) is recovered from the reaction zone by acidification and extractive methods as is known in the art. It can be purified by silica gel chromatography and recrystallization.

In step c, the carboxy functionality of the appropriate carboxy-t-butylthiomethyl disubstituted bicyclic compound of structure (3) is amidated with the appropriate amine or amino acid of structure (4) to give the N-[[2-[[(t-butyl)thio]methyl]bicyclic compound]carbonyl]-amide or amino acid of structure (5).

For example, the carboxy functionality of the appropriate carboxy-t-butylthiomethyl disubstituted bicyclic compound of structure (3) is first contacted with a molar excess of oxalyl chloride. The reactants are typically contacted in a suitable organic solvent such as methylene chloride. The reactants are typically stirred together for a period of time ranging from 1-5 hours and at a temperature range of from 0° C. to room temperature. The intermediate acid chloride is recovered from the reaction zone by evaporation of the solvent.

The intermediate acid chloride is contacted with a molar equivalent of the appropriate amine or amino acid of structure (4) and two molar equivalents of an appropriate acid scavenger such as triethylamine or sodium hydrogen carbonate. The reactants are typically contacted in a suitable organic solvent such as methylene chloride, chloroform or acetone. The reactants are typically stirred together for a period of time ranging from 30 minutes to 24 hours. The N-[[2-[[(t-butyl)thio]methyl]-bicyclic compound]carbonyl]-amide or amino acid of structure (5) is recovered from the reaction zone by extractive methods as is known in the art. It can be purified by silica gel chromatography.

Alternatively, the appropriate carboxy-t-butylthiomethyl disubstituted bicyclic compound of structure (3) is contacted with a molar equivalent of a coupling agent, such as 1-(3-dimethylaminopropyl)-3-ethylcarbodiimide hydrochloride, a molar equivalent of an appropriate amine or amino acid of structure (4) and a molar equivalent of an appropriate acid scavenger such as triethylamine. The reactants are typically contacted in a suitable organic solvent such as tetrahydrofuran. The reactants are typically stirred together at room temperature for a period of time ranging from 2-24 hours. The N-[[2-[[(t-butyl)thio]methyl]-bicyclic compound]carbonyl]-amide or amino acid of structure (5) is recovered from the reaction zone by extractive methods as is known in the art. It can be purified by silica gel chromatography.

In optional step $d_1$, the t-butylsulfide functionality of the appropriate N-[[2-[[(t-butyl)thio]methyl]-bicyclic compound]carbonyl]-amide or amino acid of structure (5), wherein Z' is phenyl substituted or unsubstituted or —COOR', wherein R' is a $C_1$-$C_4$ alkyl or benzyl ester, is cleaved to give the corresponding N-[[2-[mercaptomethyl]bicyclic compound]carbonyl]-amide or amino acid ester of structure (6).

For example, the appropriate N-[[2-[[(t-butyl)thio]methyl]-bicyclic compound]carbonyl]-amino acid of structure (5), wherein R is a $C_1$-$C_4$ alkyl or benzyl ester, is contacted with a molar equivalent of mercuric acetate. The reactants are typically contacted in an appropriate acidic solvent such as trifluoroacetic acid. The reactants are typically stirred together at room temperature for a period of time ranging from 1-24 hours. Mercury is removed from the reaction mixture by the addition of excess hydrogen sulfide. The N-[[2-[mercaptomethyl]-bicyclic compound]carbonyl]-amino acid, ester of structure (6) is recovered from the reaction zone by extractive methods as is known in the art. It can be purified by silica gel chromatography.

In optional step d2, the ester functionality of the appropriate N-[[2-[[(t-butyl)thio]methyl]-bicyclic compound]carbonyl]-amino acid of structure (5), wherein Z is —COOR and R is a $C_1$-$C_4$ alkyl or benzyl ester, is cleaved to give the corresponding N-[[2-[[(t-butyl)thio]methyl]bicyclic compound]carbonyl]-amino acid of structure (7), wherein R is hydrogen.

For example, the appropriate N-[[2-[[(t-butyl)thio]methyl]-bicyclic compound]carbonyl]-amino acid of structure (5), wherein R is a $C_1$-$C_4$ alkyl or benzyl ester, is contacted with a catalytic amount of trifluoromethanesulfonic acid. The reactants are typically contacted in an appropriate organic solvent such as dimethylsulfide. The reactants are typically stirred together at room temperature for a period of time ranging from 2-25 hours. The N-[[2-[[(t-butyl)thio]methyl]bicyclic compound]carbonyl]-amino acid of structure (7), wherein R is hydrogen can be recovered from the reaction zone by extractive methods as is known in the art. It may be purified by silica gel chromatography.

Alternatively, the ester functionality of the appropriate N-[[2-[[(t-butyl)thio]methyl]-bicyclic compound]carbonyl]-amino acid of structure (5), wherein R is a $C_1$-$C_4$ alkyl or benzyl ester, is hydrolyzed to give the corresponding N-[[2-[[(t-butyl)thio]methyl]-bicyclic compound]carbonyl]-amino acid of structure (7), wherein R is hydrogen as described previously in step b.

In optional step $e_1$, the thiol functionality of the appropriate N-[[2-[mercaptomethyl]-bicyclic compound]carbonyl]-amide or amino acid, ester of structure (6) is acylated to give the appropriate N-[[2-[(acetylthio)methyl]-bicyclic compound]carbonyl]-amide or amino acid of structure (8).

For example, the appropriate N-[[2-[mercaptomethyl]bicyclic compound]carbonyl]-amino acid, ester of structure (6) can be contacted with a molar equivalent of an appropriate acylating agent such as acetic anhydride and a catalytic amount of an acid such as sulfuric acid. The reactants are typically stirred together for a period of time ranging from 10 minutes to 10 hours. The N-[[2[(acetylthio)methyl]-bicyclic compound]carbonyl]-amino acid, ester of structure (8) can be recovered from the reaction zone by evaporation of the solvent. It can be purified by silica gel chromatography.

Alternatively, the appropriate N-[[2-[mercaptomethyl]bicyclic compound]carbonyl]-amide or amino acid, ester of structure (6 l) can be contacted with a molar equivalent of an appropriate acylating agent such as benzoyl chloride and a molar equivalent of a base such as pyridine. The reactants are typically stirred together for a period of time ranging from 10 minutes to 10 hours. The N-[[2[(benzoylthio)methyl]-bicyclic compound]carbonyl]-amide or amino acid, ester of structure (8) can be recovered fromthe reaction zone by evaporation of the solvent. It can be purified by silica gel chromatography.

In optional step $e_2$, the ester functionality of an appropriate N-[[2-[mercaptomethyl]-bicyclic compound]carbonyl]-amino acid, ester of structure (6) is hydrolyzed to give the N-[[2-[mercaptomethyl]-bicyclic compound]carbonyl]-amino acid of structure (9).

For example, the appropriate N-[[2-[mercaptomethyl]-bicyclic compound]carbonyl]-amino acid, ester of structure (6) is contacted with a molar excess of an appropriate acid such as trifluoromethanesulfonic acid. The reactants are typically contacted in a suitable nonpolar organic solvent such as dimethylsulfide. The reactants are typically stirred together for a period of time ranging from 15 minutes to 5 hours. The N-[[2-[mercaptomethyl]-biلyclic compound]carbonyl]-amino acid of structure (9) is recovered from the reaction zone by evaporatoni of the solvent. It can be purified by silica gel chromatography.

In optional step $e_3$, the t-butylsulfide functionality of the appropriate N-[[2-[[(t-butyl)thio]methyl]-bicyclic compound]carbonyl]-amino acid of structure (7), wherein R is hydrogen, is cleaved to give the corresponding N-[[2-[mercaptomethyl]-bicyclic compound]carbonyl]-amino acid of structure (9) as described previously in optional step $d_1$.

In optional step f, the thiol functionality of the appropriate N-[[2-[mercaptomethyl]-bicyclic compound]carbonyl]-amino acid of structure (7) is acylated to give the appropriate N-[[2-[(acetylthio)methyl]-bicyclic compound]carbonyl]-amino acid or N-[[2-[(benzoylthio)methyl]-bicyclic compound]carbonyl]-amino acid of structure (10) as described previously in optional step $e_1$.

Starting materials for use in Scheme A are readily available to one of ordinary skill in the art. For example, certain carbomethoxy substituted bicyclic compounds (1) are described in *J. Med. Chem.* 32 1988 1989 and t-butyl chloromethylsulfide is described in *J. Am. Chem. Soc.* 77 572 1955.

Compounds of formula (I) may also be prepared as set forth in Scheme B, wherein all substituents unless otherwise indicated are as previously defined.

resulting thiol may be acylated according to the procedure described in Scheme A, step $e_1$.

The carboxy-acetylthiomethyl disubstituted bicyclic compound of structure (3a) is then amidated to give the corresponding N-[[2-[(acetylthio)methyl]-bicyclic compound]carbonyl]-amide or amino ester of structure (8) according to the procedures set forth in Scheme A, step c.

The acetylthio functionality of the N-[[2-[(acetylthio)methyl]-bicyclic compound]carbonyl]-amide or amino acid of structure (8) may then be hydrolysed selectively to give the N-[[2-[mercaptomethyl]-bicyclic compound]carbonyl]-amide or amino acid of structure (6). This is accomplished by utilizing a reagent which will selectively hydrolyze the acetylthio moiety while not reacting with the amide or amino acid moiety. For example, the N-[[2-[(acetylthio)methyl]-bicyclic compound]carbonyl]amide or amino acid of structure (8) may be reacted with ammonium hydroxide in a polar solvent such as dioxane or methanol to give the N-[[2-[mercaptomethyl]-bicyclic compound]carbonyl]-amide

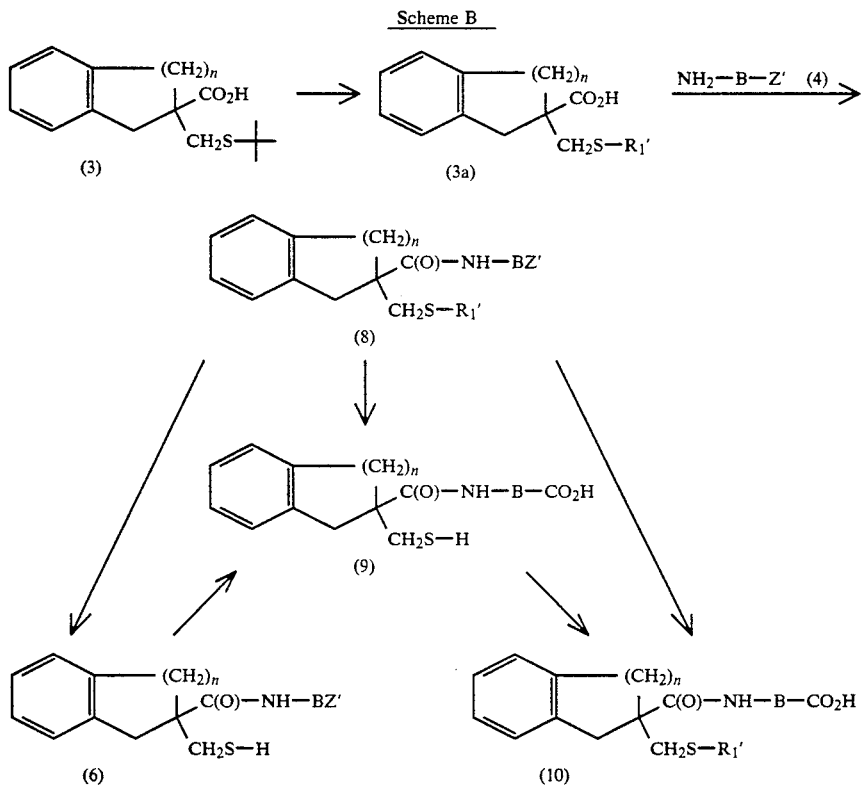

Z' = —COOR' wherein R' is $C_1$-$C_4$ alkly or benzyl, or phenyl unsubstituted or substituted
$R_1'$ = —C(O)—A Scheme B provides a general synthetic procedure for preparing compounds of formula (I). This procedure is preferred for the preparation of compounds bearing unsubstituted alcohols in the B or Z' portions of the molecule.

The t-butylsulfide functionality of the appropriate carboxy-t-butylthiomethyl disubstituted bicyclic compound of structure (3), prepared according to Scheme A, is cleaved and the thiol thus formed is acylated to give the corresponding carboxy-acetylthiomethyl disubstituted bicyclic compound of structure (3a). The t-butylsulfide functionality may be cleaved according to the procedures described in Scheme A, step $d_1$. The or amino ester of structure (6).

Where compound of structure (6) is an amino ester, it may then be further reacted to give the corresponding N-[[2-[mercaptomethyl]-bicyclic compound]carbonyl-]amino acid of structure (9) by reaction with trifluoromethanesulfonic acid as described in Scheme A, step $e_2$, or by reaction with lithium hydroxide.

The acetylthio functionality and an amide functionality of a N-[[2-[(acetylthio)methyl]-bicyclic compound]carbonyl]-amide of structure (8) may be hydrolysed at the same time to give the corresponding N-[[2-[mercaptomethyl]-bicyclic compound]carbonyl]amino acid of structure (9) by reaction with a base such as lithium hydroxide. The mercaptomethyl moiety of the N-[[2-[mercaptomethyl]-bicyclic compound]carbonyl]amino acid of structure (9) may then be acylated as described in Scheme A, step f, to give the corresponding N-[[2-[(acetylthio)methyl]-bicyclic compound]carbonyl]amino acid of structure (10).

The ester functionality of the N-[[2-[(acetylthio) methyl]-bicyclic compound]carbonyl]-amide or amino acid of structure (8) may then be hydrolysed selectively to give the corresponding N-[[2-[(acetylthio)methyl]-bicyclic compound]carbonyl]amino acid of structure (10). This is accomplished by utilizing a reagent which will selectively hydrolyze the ester moiety while not reacting with the acetylthio moiety. For example, the N-[[2-[(acetylthio)methyl]-bicyclic compound]carbonyl]-amide or amino acid of structure (8) may be reacted with trifluoromethanesulfonic acid to give the corresponding N-[[2-[(acetylthio)methyl]-bicyclic compound]carbonyl]amino acid of structure (10) as described in Scheme A, step $d_2$.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

N-[[2-(mercaptomethyl)-2,3-dihydro-1H-indene-2-yl]carbonyl]-glycine, benzyl ester

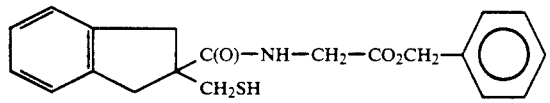

Step a: 2-Carbomethoxy-2-(t-butyl)thiomethyl-indane

Dissolve diethyl malonate (7.6 mL, 50 mmol) in anhydrous tetrahydrofuran (500 mL) and place under an argon atmosphere. Cool to 5° C., add sodium hydride (1.2 g, 50 mmol) and stir briefly until homogeneous. Add α,α'-dibromo-o-xylene (13.2 g, 50 mmol) and stir an additional 15 minutes. Add additional sodium hydride (1.2 g, 50 mmol) and stir for 16 hours while warming to room temperature. Filter, evaporate the solvent in vacuo and purify by silica gel chromatography (1:1 methylene chloride:hexane) to give 2,2-dicarbethoxy-indane (9.64 g, 74%).

Dissolve 2,2-dicarbethoxy-indane (5.67 g, 21.7 mmol) in ethanol (150 mL). Add 1N lithium hydroxide (50 mL) and stir overnight at room temperature. Reflux for 1 hour and concentrate the solution in vacuo. Partition between ethyl acetate and 6N hydrochloric acid. Separate the organic phase and wash with brine. Dry (MgSO₄) and evaporate the solvent in vacuo to give an off-white solid. Distill (120°–160° C.@0.2–0.5 mmHg) to give 2-carboxy-indane (2.5 g, 71%).

Dissolve 2-carboxy-indane (2.5 g, 15.4 mmol) in methanol and cool to 0° C. Saturate with hydrogenchloride gas then add 2,2-dimethoxypropane (2–3 mL). Stir overnight then evaporate the solvent in vacuo. Purify by silica gel chromatography (2:1 methylene chloride:hexane) to give 2-carbomethoxy-indane as a water white oil (2.04 g, 75%).

Dissolve diisopropylamine (1.09 mL, 7.8 mmol) in anhydrous tetrahydrofuran (8 mL), cool to −20° C. and place under an argon atmosphere. Add, by dropwise addition, n-butyllithium (3.12 mL of a 2.5N solution in hexanes, 7.8 mmol) and stir for 20 minutes while cooling to −70° C. Add, by dropwise addition, a solution of 2-carbomethoxyindane (1.34 g, 7.8 mmol) in anhydrous tetrahydrofuran (8 mL). Stir at −70° C. for an additional 30 minutes then add trimethylsilyl chloride (freshly distilled from barium oxide, 1.0 mL, 7.8 mmol). Allow to warm to 10° C., evaporate the solvent in vacuo and dry the residue under vacuum for 30 minutes. Suspend the residue in methylene chloride (30 mL), add zinc bromide (300 mg, 1.3 mmol) followed by t-butyl chloromethylsulfide (1.08 g, 7.8 mmol). Stir for 15 minutes at room temperature and add additional zinc bromide (500 mg, 2.2 mmol). Pour onto excess saturated sodium hydrogen carbonate and shake vigorously. Separate the organic phase and extract the aqueous phase with methylene chloride (30 mL). Combine the organic phases, dry (MgSO₄) and evaporate the solvent in vacuo give crude title compound as a brown oil (2.12 g, 98%). Purify by silica gel chromatography (30–70% methylene chloride/hexane) and recrystallize (methanol) to give the title compound as crystalline solid (1.3 g, 61%).

Step b: 2-Carboxy-2-(t-butyl)thiomethyl-indane

Dissolve 2-carbomethoxy-2-(t-butyl)thiomethyl-indane (557 mg, 2.0 mmol) in methanol (15 mL) and add 1N lithium hydroxide (3.5 mL). Warm briefly to effect solution then stir at room temperature under an argon atmosphere for 1 hour. Reflux for 6 hours, concentrate in vacuo to a volume of 3 mL and dilute to a volume of 15 mL with water. Wash with methylene chloride and acidify the aqueous phase with excess 2N hydrochloric acid. After 5 minutes, collect the resulting white precipitate by filtration and dry to give the title compound (506 mg, 96%); mp 158°–163° C.

Step c: N-[[2-[[(t-Butyl)thio]methyl]-2,3-dihydro-1H-indene-2-yl]carbonyl]-glycine, benzyl ester Dissolve 2-carboxy-2-(t-butyl)thiomethyl-indane (250 mg, 0.95 mmol) in anhydrous methylene chloride (10 mL) and add excess oxalyl chloride. Stir at room temperature for 90 minutes and add additional oxalyl chloride. Stir for 30 minutes and evaporate the solvent in vacuo to give the intermediate acid chloride as a crystalline solid.

Dissolve the intermediate acid chloride in chloroform (7 mL), add glycine benzyl ester hydrochloride (337 mg, 1.0 mmol) followed by triethylamine (0.26 mL, 2.0 mmol). Stir at room temperature for 30 minutes, wash with water, then 2N hydrochloric acid, then saturated sodium hydrogen carbonate. Dry (MgSO₄) and evaporate the solvent in vacuo to give the title compound (376 mg, 96.7%); mp 95°–97° C.

Step d₁:
N-[[2-(Mercaptomethyl)-2,3-dihydro-1H-indene-2-yl]carbonyl]-glycine, benzyl ester Dissolve N-[[2-[[(t-butyl)thio]methyl]-2,3-dihydro-1H-indene-2-yl]carbonyl]-glycine, benzyl ester (262 mg, 0.64 mmol) in trifluoroacetic acid (3 mL) and add excess anisole followed by mercuric acetate (203 mg, 0.64 mmol). Stir at room temperature for 18 hours then treat with gaseous hydrogen sulfide. Partition the mixture between methylene chloride/water (150 mL). Separate the organic phase and wash with dilute brine. Dry (MgSO₄) and evaporate the solvent in vacuo to give a clear oil. Purify by silica gel chromatography (30% ethyl acetate/hexane) to give the title compound as a crystalline solid (213 mg, 94%); mp 92°-93° C. (methylene chloride/hexane).

Anal. Calcd for $C_{20}H_{21}NO_3S$: C, 67.58; H, 5.96; N, 3.94, S; 9.02; Found: C, 67.96; H, 6.06; N, 4.04; S, 9.02.

EXAMPLE 2

N-[[2-[(Acetylthio)methyl]-2,3-dihydro-1H-indene-2-yl]carbonyl]-glycine, benzyl ester

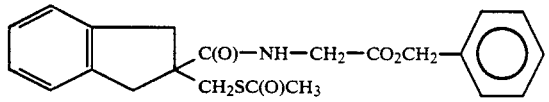

Mix N-[[2-(mercaptomethyl)-2,3-dihydro-1H-indene-2-yl]carbonyl]-glycine, benzyl ester (24.6 g, 67.2 mmol) and sulfuric acid (0.3 mL of a 10% solution in acetic acid). Add acetic anhydride (6.34 mL, 67.2 mmol) over 10 minutes. Allow to cool, pour into ethyl ether and wash with water three times. Separate the organic phase, dry (MgSO₄) and evaporate the solvent in vacuo to give the title compound.

EXAMPLE 3

N-[[2-(Mercaptomethyl)-2,3-dihydro-1H-indene-2-yl]carbonyl]-glycine

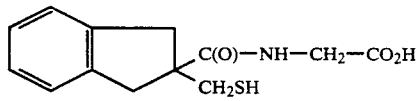

Mix N [2 (mercaptomethyl)-2,3-dihydro-1H-indene-2-yl]carbonyl]-glycine, benzyl ester (75 mg, 0.21 mmol) and 10% trifluoromethanesulfonic acid/dimethylsulfide (3 mL). Stir for 30 minutes at room temperature then dilute with ethyl ether. Remove the white precipitate by filtration and wash the filtrate with water and brine. Dry (MgSO₄) and evaporate the solvent in vacuo to give a clear oil. Purify by silica gel chromatography (methylene chloride→2:1 ethyl acetate/hexane→2:1 ethyl acetate/hexane with 5% acetic acid) to give the title compound (38 mg, 68%); mp 137°-143° C. (methylene chloride/hexane).

EXAMPLE 4

N-[[2-[(Acetylthio)methyl]-2,3-dihydro-1H-indene-2-yl]carbonyl]-glycine

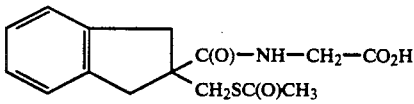

Mix N-[[2-(mercaptomethyl)-2,3-dihydro-1H-indene-2-yl]carbonyl]-glycine (17.8 g, 67.2 mmol) and sulfuric acid (0.3 mL of a 10% solution in acetic acid). Add acetic anhydride (6.34 mL, 67.2 mmol) over 10 minutes. Allow to cool, pour into ethyl ether and wash with water three times. Separate the organic phase, dry (MgSO₄) and evaporate the solvent in vacuo to give the title compound.

EXAMPLE 5

N-[[1,2,3,4-Tetrahydro-2-(mercarptomethyl)-2-naphthalenyl]carbonyl]-glycine, benzyl ester

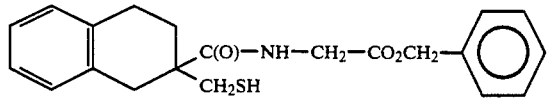

Step a:
2-Carbomethoxy-2-(t-butyl)thiomethyl-1,2,3,4-tetrahydronaphthalene

Dissolve 1,2,3,4-tetrahydro-2-naphthoic acid (10 g, 57 mmol) in methanol (100 mL) and add dimethoxypropane (3 mL). Cool to 5° C. and saturate with hydrogen chloride gas. Allow to stand overnight then evaporate the solvent in vacuo. Take the residue up in ethyl ether, wash with saturated sodium hydrogen carbonate and dry (MgSO₄). Evaporate the solvent in vacuo and distill to give 2-carbomethoxy-1,2,3,4-tetrahydronaphthalene; bp 90°-96° C.@0.25 mm Hg).

Dissolve diisopropylamine (2.31 mL, 16.5 mmol) in anhydrous tetrahydrofuran (10 mL), cool to −70° C. and place under an argon atmosphere. Add, by dropwise addition, n-butyllithium (6.6 mL of a 2.5M solution in hexane, 16.5 mmol). Stir at −70° C. for 20 minutes then add, by dropwise addition, a solution of 2-carbomethoxy-1,2,3,4-tetrahydronaphthalene (2.85 g, 15 mmol) in anhydrous tetrahydrofuran (10 mL). Stir an additional 30 minutes then add trimethylsilyl chloride (1.9 mL, 15 mmol). Evaporate the solvent in vacuo and suspend the residue in anhydrous methylene chloride (30 mL). Treat with t-butyl chloromethylsulfide (2.08 g, 15 mmol) and 3 portions of zinc bromide (300 mg each) over 15 minutes. The mixture spontaneously warms to reflux. Quickly bring to room temperature with an ice bath and wash with water then saturated sodium hydrogen carbonate. Dry (MgSO₄) and evaporate the solvent in vacuo to give a yellow oil. Purify by silica gel chromatography (30% methylene chloride/hexane then 70% methylene chloride/hexane) and recrystallize (methanol) to give the title compound (2.89 g, 65.2%).

Step b:
2-Carboxy-2-(t-butyl)thiomethyl-1,2,3,4-tetrahydronaphthalene

Dissolve 2-carbomethoxy-2-(t-butyl)thiomethyl-1,2,3,4-tetrahydronaphthalene (2.5 g, 8.6 mmol) in methanol (50 mL) and add 1N lithium hydroxide (15 mL, 15 mmol). Stir at reflux for 12 hours and at room temperature for an additional 12 hours. Dilute with water (10 mL) and concentrate in vacuo to 20 mL. Wash with ethyl ether and acidify the aqueous phase with 2N hydrochloric acid. Extract with methylene chloride (2×25 mL), dry (MgSO$_4$) and evaporate the solvent in vacuo to give the title compound as a crystalline solid (2.37 g, 99%).

Step c:
N-[[1,2,3,4-Tetrahydro-2-[[(t-butyl)thio]methyl]-2-naphthalenyl]carbonyl]-glycine, benzyl ester Dissolve 2-carboxy-2-(t-butyl)thiomethyl-1,2,3,4-tetrahydronaphthalene (997 mg, 3.58 mmol) in anhydrous methylene chloride (20 mL) and add excess oxalyl chloride. Stir at room temperature for 3 hours then evaporate the solvent in vacuo to give the intermediate acid chloride.

Dissolve the intermediate acid chloride in methylene chloride (20 mL) and add glycine benzyl ester tosylate salt followed by triethylamine (0.94 mL, 7.16 mmol). Cool briefly with an ice bath then stir overnight at room temperature. Pour into water and separate the organic phase. Wash with 2N hydrochloric acid then saturated sodium hydrogen carbonate. Dry (MgSO$_4$) and evaporate the solvent in vacuo to give 1.5 g crude product as a clear heavy oil. Purify by silica gel chromatography (25% ethyl acetate/hexane) to give the title compound as a crystalline solid (1.3 g, 85.6%).

Step d$_1$:
N[[1,2,3,4-Tetrahydro-2-(mercarptomethyl)-2-naphthalenyl]carbonyl]-glycine, benzyl ester Dissolve N-[[1,2,3,4-tetrahydro-2-[[(t-butyl)thio]methyl]-2-naphthalenyl]carbonyl]-glycine, benzyl ester (1.11 g, 2.60 mmol) in trifluoroacetic acid (10 mL) and add mercuric acetate (824 mg, 2.6 mmol). Stir at room temperature under an argon atmosphere for 4.5 hours then treat with gaseous hydrogen sulfide. Remove the resulting black solid by filtration and dilute the filtrate with methylene chloride to 100 mL volume. Wash with water then with brine and dry (MgSO$_4$). Evaporate the solvent in vacuo and purify by silica gel chromatography (20–25% ethyl acetate/hexane) to give the title compound as a heavy white oil (905 mg, 94%).

Anal. Calcd for C$_{21}$H$_{23}$NO$_3$S: C, 68.27; H, 6.27; S, 8.68; Found: C, 67.96; H, 6.31; S, 8.40.

EXAMPLE 6
N-[[1,2,3,4-Tetrahydro-2-[(acetylthio)methyl]-2-naphthalenyl]carbonyl]-glycine, benzyl ester

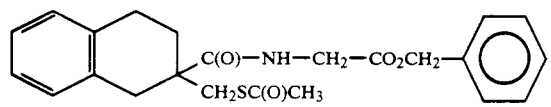

Mix N-[[1,2,3,4-tetrahydro-2-(mercarptomethyl)-2-naphthalenyl]carbonyl]-glycine, benzyl ester (2.24 g, 6.07 mmol) and sulfuric acid (0.1 mL of a 10% solution in acetic acid). Add acetic anhydride (0.572 mL, 6.07 mmol) and stir for 2 hours. Dilute with ethyl ether, wash with water then saturated sodium hydrogen carbonate and brine. Dry (MgSO$_4$) and evaporate the solvent in vacuo to give 2.2 g of a yellow oil. Purify by silica gel chromatography (5% ethyl ether/methylene chloride) to give the title compound as a light yellow oil (1.76 g, 70.4%).

EXAMPLE 7
N-[[1,2,3,4-Tetrahydro-2-(mercarptomethyl)-2-naphthalenyl]carbonyl]-glycine

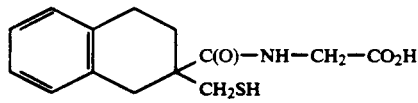

Dissolve N-[[1,2,3,4-tetrahydro-2-(mercarptomethyl)-2-naphthalenyl]carbonyl]-glycine, benzyl ester (74 mg, 0.2 mmol) in dimethylsulfide (2 mL) and add trifluoromethanesulfonic acid (0.2 mL). Stir at room temperature under an argon atmosphere for 1 hour. Dilute to a volume of 50 mL with methylene chloride and extract with brine. Dry (MgSO$_4$) and evaporate the solvent in vacuo to give 53 mg crude product. Purify by silica gel chromatography (methylene chloride then with 0.1:1:1 acetic acid:ethyl acetate:hexane) and recrystallize (methylene chloride/hexane) to give the title compound as a crystalline solid (32 mg, 50%); mp 136°–145° C.

EXAMPLE 8
N-[[1,2,3,4-Tetrahydro-2-[(acetylthio)methyl]-2-naphthalenyl]carbonyl]-glycine

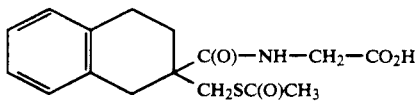

Mix N-[[1,2,3,4-tetrahydro-2-(mercarptomethyl)-2-naphthalenyl]carbonyl]-glycine (18.7 g, 67.2 mmol) and sulfuric acid (0.3 mL of a 10% solution in acetic acid). Add acetic anhydride (6.34 mL, 67.2 mmol) over 10 minutes. Allow to cool, pour into ethyl ether and wash with water three times. Separate the organic phase, dry (MgSO$_4$) and evaporate the solvent in vacuo to give the title compound.

EXAMPLE 9
N-[[1,2,3,4-Tetrahydro-2-(mercarptomethyl)-2-naphthalenyl]carbonyl]-L-valine

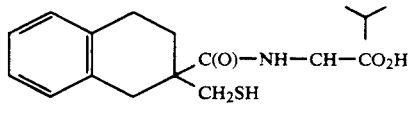

Step c:
N-[[1,2,3,4-Tetrahydro-2-[[(t-butyl)thio]methyl]-2-naphthalenyl]carbonyl]-L-valine, benzyl ester Dissolve 2-carboxy-2-(t-butyl)thiomethyl-1,2,3,4-tetrahydronaphthalene (278 mg, 1.0 mmol) in anhydrous tetrahydrofuran (10 mL). Add 1-(3-dimethylaminopropyl)-3-ethyl-carbodiimide hydrochloride (230 mg, 1.2 mmol), L-valine benzyl ester hydrochloride (244 mg, 1.00 mmol) and triethylamine (0.132 mL, 1.00 mmol). Stir at room temperature under an argon atmosphere overnight. Partition between ethyl ether and 5% sulfuric acid. Separate the organic phase and wash with water, saturated sodium hydrogen carbonate and brine. Dry (MgSO4) and evaporate the solvent in vacuo. Purify by silica gel chromatography (20% ethyl acetate/hexane) to give the title compound as a clear yellow oil (256 mg, 55%).

Optional Step d2:
N-[[1,2,3,4-tetrahydro-2-[[(t-butyl)thio]methyl]-2-naphthalenyl]carbonyl]-L-valine Dissolve N-[[1,2,3,4-tetrahydro-2-[[(t-butyl)thio]methyl]-2-naphthalenyl]carbonyl]-L-valine, benzyl ester (256 mg, 0.547 mmol) in dimethylsulfide (3 mL) and add trifluoromethanesulfonic acid (0.2 mL). Stir at room temperature under an argon atmosphere for 6 hours. Dilute with water and extract into ethyl ether. Wash with water, then brine and dry (MgSO4). Evaporate the solvent in vacuo to give the title compound.

Optional Step e3:
N-[[1,2,3,4-Tetrahydro-2-(mercarptomethyl)-2-naphthalenyl]carbonyl]-L-valine Dissolve N-[[1,2,3,4-tetrahydro-2-[[(t-butyl)thio]methyl]-2-naphthalenyl]carbonyl]-L-valine is trifluoroacetic acid (2 mL) and and mercuric acetate (175 mg, 0.547 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:10:10/acetic acid/ethyl acetate/hexane) to give the title compound as a viscous light yellow oil (138 mg, 78%).

EXAMPLE 10

N-[[1,2,3,4-Tetrahydro-2-(mercarptomethyl)-2-naphthalenyl]carbonyl]-L-alanine

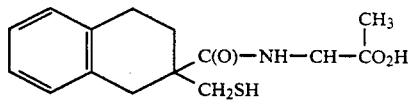

Step c:
N-[[1,2,3,4-Tetrahydro-2-[[(t-butyl)thio]methyl]-2-naphthalenyl]carbonyl]-L-alanine, benzyl ester Dissolve 2-carboxy-2-(t-butyl)thiomethyl-1,2,3,4-tetrahydronaphthalene (278 mg, 1.0 mmol) in anhydrous tetrahydrofuran (10 mL). Add 1-(3-dimethylaminopropyl)-3-ethyl-carbodiimide hydrochloride (230 mg, 1.2 mmol), L-alanine benzyl ester hydrochloride (216 mg, 1.00 mmol) and triethylamine (0.132 mL, 1.00 mmol). Stir at room temperature under an argon atmosphere overnight. Partition between ethyl ether and 5% sulfuric acid. Separate the organic phase and wash with water, saturated sodium hydrogen carbonate and brine. Dry (MgSO4) and evaporate the solvent in vacuo. Purify by silica gel chromatography (20% ethyl acetate/hexane) to give the title compound as a clear yellow oil (210 mg, 48%).

Optional Step d2:
N-[[1,2,3,4-tetrahydro-2-[[(t-butyl)thio]methyl]-2-naphthalenyl]carbonyl]-L-alanine Dissolve N-[[1,2,3,4-tetrahydro-2-[[(t-butyl)thio]methyl-2-naphthalenyl]carbonyl]-L-alanine, benzyl ester (210 mg, 0.48 mmol) in dimethylsulfide (3 mL). Add excess anisole and trifluoromethanesulfonic acid (0.5 mL). Stir at room temperature under an argon atmosphere overnight. Dilute with water and extract into ethyl ether. Wash with water, then brine and dry (MgSO4). Evaporate the solvent in vacuo to give the title compound.

Optional Step e3:
N-[[1,2,3,4-Tetrahydro-2-(mercarptomethyl)-2-naphthalenyl]carbonyl]-L-alanine Dissolve N-[[1,2,3,4-tetrahydro-2-[[(t-butyl)thio]methyl]-2-naphthalenyl]carbonyl]-L-alanine is trifluoroacetic acid (2 mL) and and mercuric acetate (175 mg, 0.547 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:10:10/acetic acid/ethyl acetate/hexane) to give the title compound as a viscous light yellow oil (138 mg, 78%).

EXAMPLE 11

N-[[1,2,3,4-Tetrahydro-2-(mercarptomethyl)-2-naphthalenyl]carbonyl]-L-leucine

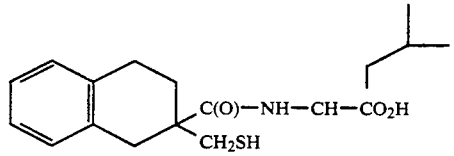

Step c:
N-[[1,2,3,4-Tetrahydro-2-[[(t-butyl)thio]methyl]-2-naphthalenyl]carbonyl]-L-leucine, methyl ester Dissolve 2-carboxy 2-(t-butyl)thiomethyl 1,2,3,4-tetrahydronaphthalene (997 mg, 3.58 mmol) in anhydrous methylene chloride (20 mL) and add excess oxalyl chloride. Stir at room temperature for 3 hours then evaporate the solvent in vacuo to give the intermediate acid chloride.

Dissolve the intermediate acid chloride (156 mg, 0.5 mmol) in anhydrous methylene chloride (2 mL). Add L-leucine methyl ester hydrochloride (91 mg, 0.5 mmol) and triethylamine (0.132 mL, 1.00 mmol). Stir at room temperature under an argon atmosphere overnight and evaporate the solvent in vacuo. Partition the residue between ethyl ether and 5% sulfuric acid. Separate the organic phase and wash with water, saturated sodium hydrogen carbonate and brine. Dry (MgSO4) and evaporate the solvent in vacuo. Purify by silica gel chromatography (1:1 ethyl acetate/hexane) to give the title compound as a clear yellow oil (145 mg, 71.5%).

Optional Step d2:
N-[[1,2,3,4-tetrahydro-2-[[(t-butyl)thio]methyl]-2-naphthalenyl]carbonyl]-L-leucine Dissolve N-[[1,2,3,4-tetrahydro-2-[[(t-butyl)thio]methyl]-2-naphthalenyl]carbonyl]-L-leucine, methyl ester (146 mg, 0.36 mmol) in methanol (3 mL). Add a solution of lithium hydroxide monohydrate (1 mL in water, 1 mmol) and stir at room temperature under argon for 16 hours. Evaporate the solvent in vacuo without heat and acidify with 2N hydrochloric acid. Extract into methylene chloride (2X), dry (MgSO₄) and evaporate the solvent in vacuo to give the title compound as as white foam (142 mg, 100%).

Optional Step e₃:
N-[[1,2,3,4-Tetrahydro-2-(mercarptomethyl)-2-naphthalenyl]carbonyl]-L-leucine Dissolve N-[[1,2,3,4-tetrahydro-2-[[(t-butyl)thio]methyl]-2-naphthalenyl]carbonyl]-L-leucine (142 mg, 0.36 mmol) in trifluoroacetic acid (2 mL) and add mercuric acetate (115 mg, 0.36 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:10:10/acetic acid/ethyl acetate/hexane) to give the title compound as a viscous light yellow oil (107 mg, 88%).

EXAMPLE 12

N-[[1,2,3,4-Tetrahydro-2-(mercarptomethyl)-2-naphthalenyl]carbonyl]-8-alanine

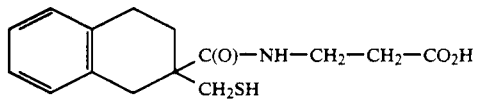

Step c:
N-[[1,2,3,4-Tetrahydro-2-[[(t-butyl)thio]methyl]-2-naphthalenyl]carbonyl]-8-alanine, methyl ester Dissolve 2-carboxy-2-(t-butyl)thiomethyl-1,2,3,4-tetrahydronaphthalene (997 mg, 3.58 mmol) in anhydrous methylene chloride (20 mL) and add excess oxalyl chloride. Stir at room temperature for 3 hours then evaporate the solvent in vacuo to give the intermediate acid chloride.

Dissolve the intermediate acid chloride (148 mg, 0.5 mmol) in anhydrous methylene chloride (5 mL). Add β-alanine methyl ester hydrochloride (60 mg, 0.5 mmol) and triethylamine (0.132 mL, 1.00 mmol). Stir at room temperature under an argon atmosphere for 45 minutes and evaporate the solvent in vacuo. Partition the residue between ethyl ether and 5% sulfuric acid. Separate the organic phase and wash with water, saturated sodium hydrogen carbonate and brine. Dry (MgSO₄) and evaporate the solvent in vacuo. Purify by silica gel chromatography (3:1 ethyl acetate/hexane) to give the title compound as a clear yellow oil (119 mg, 65%).

Optional Step d₂:
N-[[1,2,3,4-tetrahydro-2-[[(t-butyl)thio]methyl]-2-naphthalenyl]carbonyl]-β-alanine Dissolve N-[[1,2,3,4-tetrahydro-2-[[(t-butyl)thio]methyl]-2-naphthalenyl]carbonyl]-8-alanine, methyl ester (119 mg, 0.33 mmol) in methanol (3 mL). Add an aqueous solution of lithium hydroxide hydrate (1 mL, 1 mmol) and stir at room temperature under argon overnight. Evaporate the solvent in vacuo to a volume of 1 mL. Partition between 1N hydrochloric acid and methylene chloride. Separate the organic phase and extract the acidic phase with methylene chloride (2×10 mL). Combine the organic phases, dry (MgSO₄) and evaporate the solvent in vacuo to give the title compound (106 mg, 93%).

Optional Step e₃:
N-[[1,2,3,4-Tetrahydro-2-(mercarptomethyl)-2-naphthalenyl]carbonyl]-β-alanine Dissolve N-[[1,2,3,4-tetrahydro-2-[[(t-butyl)thio]methyl]-2-naphthalenyl]carbonyl]-8-alanine (106 mg, 0.30 mmol) in trifluoroacetic acid (3 mL) and add mercuric acetate (97 mg, 0.30 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:10:10/acetic acid/ethyl acetate/hexane) to give the title compound as a clear yellow film (78 mg, 88%).

EXAMPLE 13

N-[[1,2,3,4-Tetrahydro-2-(mercarptomethyl)-2-naphthalenyl]carbonyl]-L-phenylalanine Step c:
N-[[1,2,3,4-Tetrahydro-2-[[(t-butyl)thio]methyl]-2-naphthalenyl]carbonyl]-L-phenylalanine, methyl ester Dissolve 2-carboxy-2-(t-butyl)thiomethyl-1,2,3,4-tetrahydronaphthalene (997 mg, 3.58 mmol) in anhydrous methylene chloride (20 mL) and add excess oxalyl chloride.

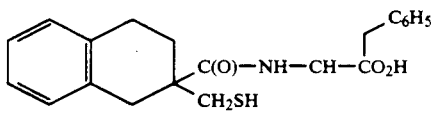

Stir at room temperature for 3 hours then evaporate the solvent in vacuo to give the intermediate acid chloride. Dissolve the intermediate acid chloride (148 mg, 0.5 mmol) in anhydrous methylene chloride (5 mL). Add L phenylalanine methyl ester hydrochloride (108 mg, 0.5 mmol) and triethylamine (0.132 mL, 1.00 mmol). Stir at room temperature under an argon atmosphere for 45 minutes and dilute with ethyl ether (50 mL). Wash with 5% sulfuric acid, then saturated sodium hydrogen carbonate (2×10 mL). Dry (MgSO₄) and evaporate the solvent in vacuo. Purify by silica gel chromatography (1:3 ethyl acetate/hexane) to give the title compound as a yellow oil (158 mg, 72%).

Optional Step d₂:
N-[[1,2,3,4-tetrahydro-2-[[(t-butyl)thio]methyl]-2-naphthalenyl]carbonyl]-L-phenylalanine Dissolve N-[[1,2,3,4-tetrahydro-2-[[(t-butyl)thio]methyl]-2-naphthalenyl]carbonyl]-L-phenylalanine, methyl ester (158 mg, 0.36 mmol) in methanol (3 mL). Add a solution of lithium hydroxide hydrate (1 mL in water, 1 mmol) and stir at room temperature under argon overnight. Partition between 1N hydrochloric acid and methylene chloride. Separate the organic phase and extract the acidic phase with methylene chloride (2×10 mL). Combine the organic phases, dry (MgSO₄) and evaporate the solvent in vacuo to give the title compound (149 mg, 97%).

Optional Step e₃:
N-[[1,2,3,4-Tetrahydro-2-(mercarptomethyl)-2-naphthalenyl]carbonyl]-L-phenylalanine Dissolve N-[[1,2,3,4-tetrahydro-2-[[(t-butyl)thio]methyl]-2-naphthalenyl]carbonyl]-L-phenylalanine (149 mg, 0.35 mmol) in trifluoroacetic acid (3 mL) and add mercuric acetate (111 mg, 0.35 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:8:12/acetic acid/ethyl acetate/hexane) to give the title compound as a viscous light yellow oil (121 mg, 94%).

EXAMPLE 14
8-[[[1,2,3,4
Tetrahydro-2-(mercarptomethyl)-2-naphthalenyl]carbonyl]amino]-octanoic acid

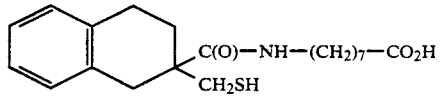

Step c:
7-[[[1,2,3,4-Tetrahydro-2-[[(t-butyl)thio]methyl]-2-naphthalenyl]carbonyl]amino]-heptanoic acid Dissolve 2-carboxy-2-(t-butyl)thiomethyl-1,2,3,4-tetrahydronaphthalene (997 mg, 3.58 mmol) in anhydrous methylene chloride (20 mL) and add excess oxalyl chloride. Stir at room temperature for 3 hours then evaporate the solvent in vacuo to give the intermediate acid chloride.

Dissolve the intermediate acid chloride (200 mg, 0.67 mmol) in acetone (3 mL). Add a solution of 7-amino heptanoic acid hydrochloride (120 mg, 0.67 mmol) in saturated sodium hydrogen carbonate. Stir at room temperature under an argon atmosphere for 30 minutes. Partition the residue between methylene chloride and 2N hydrochloric acid. Separate the organic phase and wash with water, saturated sodium hydrogen carbonate and brine. Dry (MgSO₄) and evaporate the solvent in vacuo. Purify by silica gel chromatography (1:4:15 acetic acid/ethyl acetate/hexane) to give the title compound as a clear yellow oil (140 mg, 52%).

Optional Step e₃:
7-[[[1,2,3,4-Tetrahydro-2-(mercarptomethyl)-2-naphthalenyl]carbonyl]amino]-heptanoic acid Dissolve 7-[[[1,2,3,4-tetrahydro-2-[[(t-butyl)thio]methyl]-2-naphthalenyl]carbonyl]amino]-heptanoic acid (140 mg, 0.345 mmol) in trifluoroacetic acid (3 mL) and add mercuric acetate (110 mg, 0.345 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:6:15/acetic acid/ethyl acetate/hexane) to give the title compound as a viscous light yellow oil (101 mg, 84%).

EXAMPLE 15
4-[[[1,2,3,4-Tetrahydro-2-(mercarptomethyl)-2-naphthalenyl]carbonyl]amino]-cis-cyclohexanecarboxylic acid

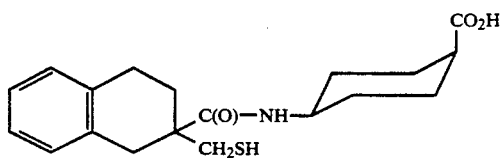

Step c:
4-[[[1,2,3,4-Tetrahydro-2-[[(t-butyl)thio]methyl]-2-naphthalenyl]carbonyl]amino]-cis-cyclohexanecarboxylic acid Suspend 5% rhodium/carbon (2 g) in water (50 mL) and add 4-aminobenzoic acid (27.4 g, 200 mmol) and dilute to 200 mL with water. Shake the mixture at 50 psi for 4 days, filter through glass fiber and evaporate the solvent in vacuo to a white solid. Mix the solid with diphenyl ether and heat quickly to reflux for 20 minutes. Cool and partition between hexane and water. Separate the organic phase and wash with water. Combine the aqueous phases, treat with sodium hydrogen carbonate and subject to continuous extraction with methylene chloride overnight. Evaporate the methylene chloride extracts in vacuo to give 3-isoquinuclidone as a white solid.

Dissolve 3-isoquinuclidone (1.5 g) in methanol (50 mL) and saturated with HCl. Let stand overnight then warm to reflux for 16 hours. Evaporate the solvent in vacuo to give cis-4-amino-cyclohexanecarboxylic acid, methyl ester hydrochloride as a white foam.

Dissolve cis-4-amino-cyclohexanecarboxylic acid, methyl ester hydrochloride (1.5 g) in water (5 mL) and add concentrated hydrochloric acid (5 mL). Reflux under an argon atmosphere for 12 hours and evaporate the solvent in vacuo to give cis-4-amino-cyclohexanecarboxylic acid hydrochloride.

Dissolve 2-carboxy-2-(t-butyl)thiomethyl-1,2,3,4-tetrahydronaphthalene (997 mg, 3.58 mmol) in anhydrous methylene chloride (20 mL) and add excess oxalyl chloride. Stir at room temperature for 3 hours then evaporate the solvent in vacuo to give the intermediate acid chloride.

Dissolve cis-4-amino-cyclohexanecarboxylic acid hydrochloride (121 mg, 0.67 mmol) in saturated sodium hydrogen carbonate (3 mL). Add a solution of the the intermediate acid chloride (200 mg, 0.67 mmol) in acetone (3 mL) and stir at room temperature under an argon atmosphere for 30 minutes. Partition the residue between methylene chloride and 2N hydrochloric acid. Separate the organic phase, dry (MgSO₄) and evaporate the solvent in vacuo. Purify by silica gel chromatography (1:5:15 acetic acid/ethyl acetate/hexane) to give the title compound as a white crystalline solid (160 mg, 59%).

Optional Step e₃:
4-[[[1,2,3,4-Tetrahydro-2-(mercarptomethyl)-2-naphthalenyl]carbonyl]amino]-cis-cyclohexanecarboxylic acid Dissolve 4-[[[1,2,3,4-tetrahydro-2-[[(t-butyl)thio]methyl]2-naphthalenyl]carbonyl]amino]-cis-cyclohexanecarboxylic acid (160 mg, 0.40 mmol) in trifluoroacetic acid (3 mL) and add mercuric acetate (126 mg, 0.40 mmol). Stir at room temperature under an argon atmosphere overnight. Saturate the resulting solution with hydrogen sulfide, filter and wash with methylene chloride. Concentrate the filtrate in vacuo and purify by silica gel chromatography (1:4:15/acetic acid/ethyl acetate/hexane) to give the title compound as a white foam (130 mg, 94%).

EXAMPLE 16

N-[[1,2,3,4-Tetrahydro-2-[(acetylthio)methyl]-2-naphthalenyl]carbonyl]-isoserine, benzyl ester

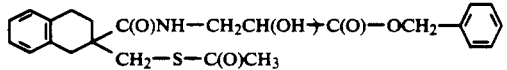

2-Carboxy-2-[(acetylthio)methyl]-1,2,3,4-tetrahydronaphthalene

Dissolve 2-carboxy-2-(t-butyl)thiomethyl-1,2,3,4-tetrahydronaphthalene (5.36 g, 20.0 mmol) in trifluoroacetic acid (40 mL) and add mercuric acetate (6.36 g, 20.0 mmol). Stir at ambient temperature under an atmosphere of argon for 4.5 hours, then treat with gaseous hydrogen sulfide. Remove the resulting black solid by filtration and dilute the filtrate to 100 mL with methylene chloride. Wash with water, then with brine and dry (MgSO$_4$). Evaporate the solvent in vacuo to a residue. Mix the residue with sulfuric acid (0.3 mL of 10% solution in acetic acid) and add acetic anhydride (2.04 g, 20.0 mmol). Stir the mixture for 2 hours under an atmosphere of argon at ambient temperature, then dilute with 100 mL ethyl ether. Wash with water, brine then dry (MgSO$_4$). Concentrate the filtrate in vacuo to give the title compound.

N-[[1,2,3,4-Tetrahydro-2-[(acetylthio)methyl]-2-naphthalenyl]carbonyl]-isoserine, benzyl ester Dissolve 2-carboxy-2-[(acetylthio)methyl]-1,2,3,4-tetrahydronaphthalene (2.88 g, 10.0 mmol) in dry dimethylformamide (20 mL). To this solution add N-methyl morpholine (1.01 g, 10.0 mmol), isoserine benzyl ester tosylate salt (3.67 g, 10.0 mmol) and 1-(3-dimethylaminopropyl)-3-ethylcarbodiimide hydrochloride (1.92 g, 10.0 mmol). Stir the reaction mixture for 18 hours under an atmosphere of argon at ambient temperature then partition between ethyl acetate and dilute HCl. Wash the organic solution with water, saturated sodium hydrogen carbonate then brine. Dry the solution (MgSO$_4$) and concentrate in vacuo. Purify the residue by column chromatography (ethyl acetate:hexane) to give the title compound.

EXAMPLE 17

N-[[1,2,3,4-Tetrahydro-2-(mercaptomethyl)-2-naphthalenyl]carbonyl]-isoserine

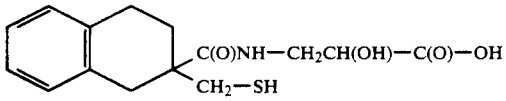

Dissolve N-[[1,2,3,4-tetrahydro-2-[(acetylthio)methyl]-2-naphthalenyl]carbonyl]-isoserine, benzyl ester (4.41 g, 10.0 mmol) in deoxygenated tetrahydrofuran (50 mL). To this solution add 1N LiOH (30 mL, 30.0 mmol) and stir under an atmosphere of argon for 4 hours. Concentrate the solution in vacuo then purify the residue by column chromatography (acetic acid:ethyl acetate:hexane) to give the title compound.

EXAMPLE 18

N-[[1,2,3,4-Tetrahydro-2-(mercaptomethyl)-2-naphthalenyl]carbonyl]-isoserine, benzyl ester

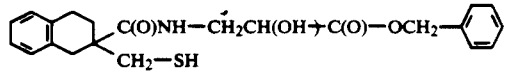

Dissolve N-[[1,2,3,4-tetrahydro-2-[(acetylthio)methyl]-2-naphthalenyl]carbonyl]-isoserine, benzyl ester (882 mg, 2.00 mmol) in tetrahydrofuran (20 mL) then add NH$_4$OH (1 mL). Stir at ambient temperature under an atmosphere of argon for 24 hours, then concentrate in vacuo. Purify the residue by column chromatography (ethyl acetate:hexane) to give the title compound.

EXAMPLE 19

N-[[1,2,3,4-Tetrahydro-2-[(acetylthio)methyl]-2-naphthalenyl]carbonyl]-isoserine

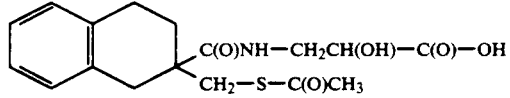

Dissolve N-[[1,2,3,4-tetrahydro-2-[(acetylthio)methyl]-2-naphthalenyl]carbonyl]-isoserine, benzyl ester (882 mg, 2.00 mmol) in dimethylsulfide (2 mL) and add trifluoromethane sulfonic acid (0.2 mL). Stir at ambient temperature under an atmosphere of argon for 1 hour. Dilute to a volume of 50 mL with methylene chloride and extract with brine. Dry (MgSO$_4$) and evaporate the solvent in vacuo to give the crude product. Purify the residue by column chromatography (acetic acid:ethyl acetate:hexane) to give the title compound.

EXAMPLE 20

N-[[1,2,3,4-Tetrahydro-2-[(acetylthio)methyl]-2-naphthalenyl]carbonyl]-3,4-dihydroxybenzylamide

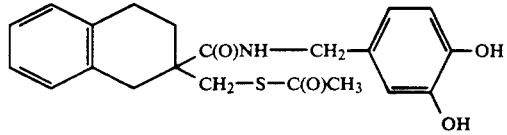

Dissolve 2carboxy-2-[(acetylthio)methyl]-1,2,3,4-tetrahydronaphthalene (2.88 g, 10.0 mmol) in dry methylene chloride (20 mL). To this solution add piperonyl amine (1.39 g, 10.0 mmol) and 1-(3-dimethylaminopropyl)-3-ethylcarbodiimide hydrochloride (1.92 g, 10.0 mmol). Stir the reaction mixture for 18 hours under an atmosphere of argon at ambient temperature, then partition between ethyl acetate and dilute HCl. Wash the organic solution with water, saturated sodium hydrogen carbonate, then brine. Dry the solution (MgSO$_4$) and concentrate in vacuo. Purify the residue by column chromatography (ethyl acetate:hexane) to give the title compound.

EXAMPLE 21

N-[[1,2,3,4-Tetrahydro-2-(mercapto)methyl-2-naphthalenyl]carbonyl]-3,4-dihydroxybenzylamide

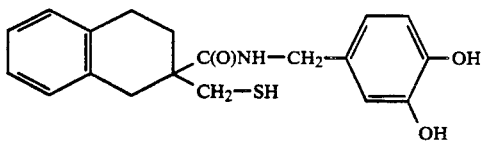

Dissolve N-[[1,2,3,4-tetrahydro-2-[(acetylthio)methyl]-2-naphthalenyl]carbonyl]-piperonylamide (1.92 g, 5.00 mmol) in deoxygenated tetrahydrofuran. To this solution add 1N LiOH (10.0 mL, 10.0 mmol) and stir under an atmosphere of argon for 4 hours. Partition between ethyl acetate and dilute HCl, wash with water and brine, dry (MgSO$_4$) then concentrate in vacuo. Purify the residue by column chromatography (ethyl acetate:hexane) to give the title compound.

In a further embodiment, the present invention provides a method of inhibiting enkephalinase in a patient in need thereof comprising administering to said patient an effective enkephalinase inhibitory amount of a compound of formula (I).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect or is in need of an antidiarrheal effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP.

In addition, a patient is in need of treatment to inhibit enkephalinase when the patient is in need of an antidepressant effect or a reduction in severity of withdrawal symptoms associated with termination of opiate or morphine administration.

A patient is also in need of treatment to inhibit enkephalinase when the patient is in need of an cognition enhancing effect due to a disease state such as Alzheimer's Disease.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect, an antidiarrheal effect, a cognition enhancing effect or an ANP-mediated diuretic, natriuretic, hypotensive or hypoaldosteronemic effect.

An effective enkephalinase inhibitory amount of a compound of formula (I) is an amount which is effective in inhibiting enkephalinase and in thus inhibiting the metabolic degradation of the naturally-occurring circulating regulatory peptides such as the endorphins, including enkephalins and ANP. Successful treatment is also understood to include prophylaxis in treating a patient in those instances such as, for example, in a preoperative procedure, where a patient will be suffering from acute or chronic pain in the near future.

An effective enkephalinase inhibitory amount of a compound of formula (I) is an amount which is effective in inhibiting enkephalinase in a patient in need thereof which results, for example, in endorphin- or enkephalin-mediated analgesic effects, an antidiarrheal effect, a cognition enhancing effect or an ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of formula (I) will generally vary from about 0.01 milligram per kilogram of body weight per day (mg/kg/day) to about 20 mg/kg/day. A daily dose of from about 0.1 mg/kg to about 10 mg/kg is preferred.

In effecting treatment of a patient, compounds of formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (I) can be administered in the form of pharmaceutical compositions or medicaments which are made by combining the compounds of formula (I) with pharmaceutically acceptable carriers or excipients, the proportion and nature of which are determined by the chosen route of administration, and standard pharmaceutical practice.

In another embodiment, the present invention provides compositions comprising a compound of formula (I) in admixture or otherwise in association with one or more inert carriers. These compositions are useful, for example, as assay standards, as convenient means of making bulk shipments, or as pharmaceutical compositions. An assayable amount of a compound of formula (I) is an amount which is readily measurable by standard assay procedures and techniques as are well known and appreciated by those skilled in the art. Assayable amounts of a compound of formula (I) will generally vary from about 0.001% to about 75% of the composition by weight. Inert carriers can be any material which does not degrade or otherwise covalently react with a compound of formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (I) may be incorporated with excipients and used in the form of tablets, troches, capsules, elixirs, suspensions, syrups, wafers, chewing gums and the like. These preparations should contain at least 4% of the compound of formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (I) in their end-use application.

The compounds of formula (I) wherein n is 2 are preferred. The compounds of formula (I) wherein B is —(CH$_2$)$_m$—CH(R$_2$)— are preferred. Compounds of formula (I) wherein m is 0 are preferred and compounds of formula (I) wherein B is a group represented by

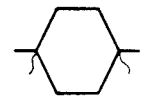

are preferred.

The following specific compounds of formula (I) are particularly preferred in the end-use application of the compounds of the present invention:

N-[[1,2,3,4-Tetrahydro-2-(mercarptomethyl)-2-naphthalenyl]carbonyl]-glycine, benzyl ester;

N-[[1,2,3,4-Tetrahydro-2-[(acetylthio)methyl]-2-naphthalenyl]carbonyl]-glycine, benzyl ester;

N-[[1,2,3,4-Tetrahydro-2-(mercarptomethyl)-2-naphthalenyl]carbonyl]-glycine;

N-[[1,2,3,4-Tetrahydro-2-[(acetylthio)methyl]-2-naphthalenyl]carbonyl]-glycine;

N-[[1,2,3,4-Tetrahydro-2-(mercarptomethyl)-2-naphthalenyl]carbonyl]-L-valine;

N-[[1,2,3,4-Tetrahydro-2-(mercarptomethyl)-2-naphthalenyl]carbonyl]-L-alanine;

N-[[1,2,3,4-Tetrahydro-2-(mercarptomethyl)-2-naphthalenyl]carbonyl]-L-leucine;

N-[[1,2,3,4-Tetrahydro-2-(mercarptomethyl)-2-naphthalenyl]carbonyl]-8-alanine;

N-[[1,2,3,4-Tetrahydro-2-(mercarptomethyl)-2-naphthalenyl]carbonyl]-L-phenylalanine;

8-[[[1,2,3,4-Tetrahydro-2-(mercarptomethyl)-2-naphthalenyl]carbonyl]amino]-heptanoic acid;

4-[[[1,2,3,4-Tetrahydro-2-(mercarptomethyl)-2-naphthalenyl]carbonyl]amino]-cis-cyclohexanecarboxylic acid.

N-[[1,2,3,4-Tetrahydro-2-[(acetylthio)methyl]-2-naphthalenyl]carbonyl]-isoserine, benzyl ester N-[[1,2,3,4-Tetrahydro-2-(mercaptomethyl)-2-naphthalenyl]carbonyl]-isoserine N-[[1,2,3,4-Tetrahydro-2-(mercaptomethyl)-2-naphthalenyl]carbonyl]-isoserine, benzyl ester N-[[1,2,3,4-Tetrahydro-2-[(acetylthio)methyl]-2-naphthalenyl]carbonyl]-isoserine N-[[1,2,3,4-Tetrahydro-2-[(acetylthio)methyl]-2-naphthalenyl]carbonyl]-3,4-dihydroxybenzylamide N-[[1,2,3,4-Tetrahydro-2-(mercapto)methyl-2-naphthalenyl]carbonyl]-3,4-dihydroxybenzylamide.

The following studies illustrate the utility of the compounds of the present invention as enkephalinase inhibitors.

Enkephalinase is partially purified from rat kidney. The enzyme is extracted from the microvilli fraction by using Triton X-100 according to the method of Malfroy and Schwartz [*J. Biol. Chem.* 259, 14365-14370 (1984)] or by using a proteolytic treatment according to the method of Almenoff and Orlowski [*Biochem.* 22, 590-599 (1983)]. The enzyme is further purified by anion exchange chromatography (Mono Q ™ column, Pharmacia) using a Pharmacia FPLC system. The enzyme activity may be measured by the fluorometric methods of Florentin et al. [*Anal. Biochem.* 141, 62-69 (1984)] or of Almenoff and Orlowski [*J. Neurochemistry* 42, 151-157 (1984)]. The enzyme is assayed in 50 mM HEPES buffer (pH 7.4) in a 3.0 mL reaction volume containing 12 μM of the substrate dansyl-D-AlaGly(p-nitro)PheGly (Km=40 μM) at 25° C. The substrate (and inhibitor) is added from a concentrated stock solution in DMSO (up to 0.1 mL DMSO final volume). The enzyme in a small volume (approximately 0.1 μg of FPLC purified protein) is added to initiate the reaction and the rate of fluorecense increase is recorded continuously using a fluorometer (excitation at 339 nm, emission at 562 nm).

The results of the analysis of enzymatic activity as described in Table 1 indicate that the compounds of the present invention are inhibitors of enkephalinase.

TABLE 1

Ki's of Compounds of Formula (1) as Inhibitors of Enkephalinase

| Compound | Enkephalinase, Ki (nM) |
|---|---|
| 100,250 | 0.4 |
| 101,890 | 0.3 |
| 101,782 | 2.0 |
| 100,552 | 0.6 |
| 100,185 | ≦0.2 |

100,250 = N-[[1,2,3,4-Tetrahydro-2-(mercarptomethyl)-2-naphthalenyl]carbonyl]-glycine
101,890 = N-[[1,2,3,4-Tetrahydro-2-(mercarptomethyl)-2-naphthalenyl]carbonyl]-L-alanine
101,782 = N-[[1,2,3,4-Tetrahydro-2-(mercarptomethyl)-2-naphthalenyl]carbonyl]-L-valine
100,552 = 4-[[[1,2,3,4-Tetrahydro-2-(mercarptomethyl)-2-naphthalenyl]carbonyl]amino]-cis-cyclohexanecarboxylic acid
100,185 = N-[[1,2,3,4-Tetrahydro-2-(mercarptomethyl)-2-naphthalenyl]carbonyl]-β-alanine

What is claimed is:

1. A compound of the formula $$\text{[structure: benzene ring fused to cyclohexane bearing } (CH_2)_n\text{—C(O)—NH—B—Z and } CH_2\text{—S—R}_1 \text{]}$$

wherein
n is an integer 2,
Z is the radical —C(O)OR, or a phenyl group unsubstituted or substituted with from 1 to 3 substituents selected from the group consisting of OH, $C_1$-$C_4$ alkoxy, and methylenedioxy,
R is H, $C_1$-$C_4$ alkyl, or benzyl,
$R_1$ is H or —C(O)—A, wherein A is $C_1$-$C_4$ alkyl, or phenyl, and
B is a radical of the formula $$-(CH_2)_m-\underset{\underset{R_2}{|}}{CH}-$$

or

-continued $$\text{[cyclohexane ring with H substituents]}$$

wherein
m is an integer 0 to 5, and
$R_2$ is H, $C_1$-$C_4$ alkyl, —$CH_2$—OH, —CH(OH)—$CH_3$, —$CH_2CH_2SCH_3$, phenylmethyl, 4-hydroxy-phenylmethyl or OH, with the proviso that $R_2$ cannot be OH when m is 0.

2. A compound according to claim 1 wherein n is 1.
3. A compound according to claim 1 wherein n is 2.
4. A compound according to claim 3 wherein B is $$-(CH_2)_m-\underset{\underset{R_2}{|}}{CH}-$$

5. A compound according to claim 4 wherein m is 0.
6. A compound according to claim 4 wherein m is 1.
7. A method of inhibiting enkephalinase in a patient in need thereof comprising administering to said patient an effective enkephalinase inhibitory amount of a compound of claim 1.
8. A method according to claim 7 wherein the patient is in need of an endorphin- or enkephalin-mediated analgesic effect.
9. A method according to claim 7 wherein the patient is in need of an ANP-mediated hypotensive effect.
10. A method according to claim 7 wherein the patient is in need of an ANP-mediated diuretic effect.
11. A method according to claim 7 wherein the patient is in need of an antidiarrheal effect.
12. A method according to claim 7 wherein the patient is suffering from Alzheimer's Disease.
13. A composition comprising an assayable amount of a compound of claim 1 in admixture or otherwise in association with an inert carrier.
14. A pharmaceutical composition comprising an effective immunosuppressive amount of a compound of claim 1 in admixture or otherwise in association with one or more pharmaceutically acceptable carriers or excipients.
15. A compound of claim 1 wherein the compound is N-[[1,2,3,4-Tetrahydro-2-(mercarptomethyl)-2-naphthalenyl]carbonyl]-glycine.
16. A compound of claim 1 wherein the compound is N-[[1,2,3,4-Tetrahydro-2-(mercarptomethyl)-2-naphthalenyl]carbonyl]-L-alanine.
17. A compound of claim 1 wherein the compound is N-[[1,2,3,4-Tetrahydro-2-(mercarptomethyl)-2-naphthalenyl]carbonyl]-L-valine.
18. A compound of claim 1 wherein the compound is 4[[[1,2,3,4-Tetrahydro-2-(mercarptomethyl)-2-naphthalenyl]carbonyl]amino]-cis-cyclohexanecarboxylic acid.
19. A compound of claim 1 wherein the compound is N-[[1,2,3,4-tetrahydro-2-(mercarptomethyl)-2-naphthalenyl]carbonyl]-β-alanine.
20. A compound of claim 1 wherein the compound is N-[[1,2,3,4-Tetrahydro-2-(mercapto)methyl-2-naphthalenyl]carbonyl]-3,4-dihydroxybenzylamide.
21. A compound of claim 1 wherein the compound is N-[[1,2,3,4-tetrahydro-2-[(acetylthio)methyl]-2-naphthalenyl]carbonyl]-3,4-dihydroxybenzylamide.

22. A compound of claim 1 wherein the compound is N-[[1,2,3,4-Tetrahydro-2-(mercaptomethyl)-2-naphthalenyl]carbonyl]-isoserine.

23. A compound of claim 1 wherein the compound is N-[[1,2,3,4-Tetrahydro-2-(mercaptomethyl)-2-naphthalenyl]carbonyl]-isoserine, benzyl ester.

24. A compound of claim 1 wherein the compound is N-[[1,2,3,4-Tetrahydro-2-[(acetylthio)methyl]-2-naphthalenyl]carbonyl]-isoserine.

25. A compound of claim 1 wherein the compound is N-[[1,2,3,4-Tetrahydro-2-[(acetylthio)methyl]-2-naphthalenyl]carbonyl]-isoserine, benzyl ester.

* * * * *

UNITED STATES PATENT AND TRADEMARK OFFICE
CERTIFICATE OF CORRECTION

Page 1 of 2

PATENT NO. : 5,252,601
DATED : October 12, 1993
INVENTOR(S) : Gary A. Flynn, et. al.

It is certified that error appears in the above-indentified patent and that said Letters Patent is hereby corrected as shown below:

Title page, under Foreign Patent Documents, insert --
0249223   12/1988      European Pat. Off.
9109840  6/1991        European Pat. Off.  --
0249224 12/1987 European Pat. Off.

Column 2, Line 40 - 45, patent structure reads:

" 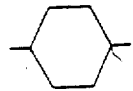 " and should read -- 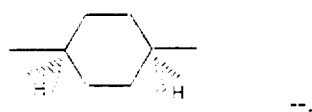 --.

Column 3, Line 40 - 45, patent structure reads:

" 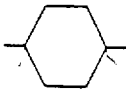 " and should read --  --.

Column 8, Line 40, patent reads: " (6 I)" and should read -- (6) --.
Column 8, Line 47, patent reads: " fromthe " and should read -- from the --.
Column 12, Line 29, patent reads: " in vacuo give " and should read -- *in vacuo* to give --.
Column 18, Line 20, patent reads: " and and " and should read -- and --.
Column 20, Line 10, patent reads: " -8-alanine " and should read -- -β-alanine --.
Column 22, Line 52, patent reads: " the the " and should read -- the --.
Column 24, Line 55, patent reads: " 2carboxy " and should read -- 2-carboxy --.
Column 25, Line 54, patent reads: " an cognition " and should read -- a cognition --.

UNITED STATES PATENT AND TRADEMARK OFFICE
CERTIFICATE OF CORRECTION

PATENT NO. : 5,252,601
DATED : October 12, 1993
INVENTOR(S) : Gary A. Flynn, et. al.

It is certified that error appears in the above-indentified patent and that said Letters Patent is hereby corrected as shown below:

Column 28, Line 25, patent structure reads:

Column 30, Line 1 - 6, patent structure reads:

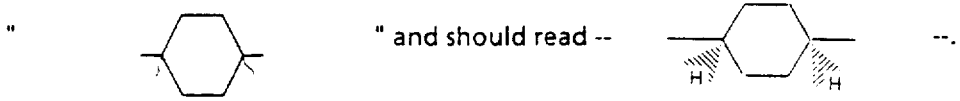

Signed and Sealed this

Thirtieth Day of January, 1996

Attest:

BRUCE LEHMAN

*Attesting Officer*          *Commissioner of Patents and Trademarks*